United States Patent
Kim et al.

(10) Patent No.: US 9,650,670 B2
(45) Date of Patent: May 16, 2017

(54) CAPACITIVE FEEDBACK (TRANSIMPEDANCE) AMPLIFIER

(71) Applicant: The Regents of the University of California, Oakland, CA (US)

(72) Inventors: Jungsuk Kim, Santa Cruz, CA (US); William Dunbar, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 75 days.

(21) Appl. No.: 14/438,868

(22) PCT Filed: Oct. 28, 2013

(86) PCT No.: PCT/US2013/067132
§ 371 (c)(1),
(2) Date: Apr. 27, 2015

(87) PCT Pub. No.: WO2014/066909
PCT Pub. Date: May 1, 2014

(65) Prior Publication Data
US 2015/0337367 A1    Nov. 26, 2015

Related U.S. Application Data

(60) Provisional application No. 61/719,443, filed on Oct. 28, 2012.

(51) Int. Cl.
H03F 3/52 (2006.01)
C12Q 1/68 (2006.01)
H03F 3/45 (2006.01)
G01N 27/447 (2006.01)
H03F 1/34 (2006.01)

(52) U.S. Cl.
CPC ......... *C12Q 1/6869* (2013.01); *G01N 27/447* (2013.01); *H03F 3/45076* (2013.01); *H03F 3/45475* (2013.01); *H03F 1/34* (2013.01); *H03F 3/45* (2013.01); *H03F 2200/261* (2013.01); *H03F 2200/411* (2013.01); *H03F 2203/45336* (2013.01); *H03F 2203/45411* (2013.01); *H03F 2203/45512* (2013.01); *H03F 2203/45528* (2013.01)

(58) Field of Classification Search
CPC ...... G01N 27/447; H03G 3/12; H03G 1/0088; H03G 11/002; H03F 3/45076; H03F 3/45475; H03F 1/38; H03F 1/34; H03F 2200/261; H03F 2203/45138; H03F 3/45; H03F 1/36
USPC ............ 330/69, 86, 109, 110, 282, 294, 308
See application file for complete search history.

(56) References Cited

U.S. PATENT DOCUMENTS

| | | | |
|---|---|---|---|
| 6,448,856 B2 * | 9/2002 | Noro ............... | H03G 3/001 330/69 |
| 6,809,313 B1 * | 10/2004 | Gresham ......... | H01J 49/40 250/283 |
| 6,838,935 B2 * | 1/2005 | Suzuki ............ | H03F 1/26 330/69 |
| 7,227,409 B2 * | 6/2007 | Chung ............ | H03F 1/34 330/260 |

(Continued)

*Primary Examiner* — Khanh V Nguyen
(74) *Attorney, Agent, or Firm* — Adam Warwick Bell; Matthew Rupert Kaser

(57) ABSTRACT

A polynucleotide sequencer comprising an integrated and multiplexed network of patch clamp capacitive integrator-differentiator amplifiers with small feedback capacitors using pseudo-resistors.

13 Claims, 13 Drawing Sheets

(56) References Cited

U.S. PATENT DOCUMENTS

| | | | | |
|---|---|---|---|---|
| 7,683,710 B2* | 3/2010 | Arnold | ............... | G10H 3/187 330/110 |
| 2004/0130326 A1* | 7/2004 | Yamamoto | ............ | B60L 3/0023 324/503 |
| 2011/0260788 A1* | 10/2011 | Inukai | .................... | H03F 3/005 330/69 |

* cited by examiner

CAPACITIVE FEEDBACK (TRANSIMPEDANCE) AMPLIFIER

RELATIONSHIP TO OTHER APPLICATIONS

This application claims the benefit of U.S. Provisional Application No. 61/719,443, entitled "Multiplexing Electronic Configuration for Multichannel Nanopore Sensing," which was filed Oct. 28, 2012.

STATEMENT OF SUPPORT

This invention was made with government support under NSF Contract/grant No. ECCS-0845766 awarded by the National Science Foundation. The government has certain rights in this invention.

FIELD OF THE INVENTION

The presently disclosed subject matter is directed towards high density multiplex nanopore sensing, for use in, for example, high-throughput sequencing.

BACKGROUND

Nanopore sequencing technology allows one to measure the ionic current generated by a molecule moving across the nanopores thereby identifying the molecule. An ionic current is a current generated by the flow of ions. In particular, nanopore sequencing enables sequencing individual nucleotide bases. Nanopore sequencing technology can also be applied to a polynucleotide or a polypeptide. Examples of polynucleotides includes, but not limited to, a double-stranded DNA, single stranded DNA, double-stranded RNA, single-stranded RNA, or DNA-RNA hybrid. For example, DNA bases from a DNA strand can be sequenced with the nanopore sequencing without any modification to that strand. The nanopore channels can be fabricated either by inserting a protein channel into a lipid membrane or by fabricating "solid-state" nanopores in a semiconductor substrate such as silicon or silicon nitride. Based on modern semiconductor fabrication technology, solid-state nanopores can enable DNA sensing at relatively low cost.

Nanopore sequencing is based on the use of nanopore sensors. A nanopore sensor has two chambers, referred to as a cis and a trans chamber that are connected by a very small channel called a nanopore. To induce the DNA being sequenced to enter the nanopore, a voltage is induced across the sensor. The chambers are filled with a buffered ionic conducting solution (e.g. KCl, CaCl2, NaCl etc.). The conducting solution and the applied voltage create an ionic current. Negatively charged DNA in the cis chamber starts moving towards the trans side. As it traverses the nanopore the ionic current, which is in the range of tens to hundreds of picoAmperes, is modulated by the DNA bases. The DNA base modulated current can be sensed and analyzed to implement an electrical DNA sequencing method.

Nanopore sequencing currents are in the tens to hundreds of picoAmperes, and therefore practical, commercial nanopore sequencing systems require very low noise at very high gains. More cost-effective and space-effective designs are desirable. Submicron CMOS technology makes it theoretically possible to miniaturize multiple nanopore measuring instrumentation by making it on a semiconductor substrate.

Accurately measuring ultra-low current variations requires patch-clamps with very high gain. Patch clamp amplifiers usually take the form of differential op-amp transimpedance amplifiers that use either resistive or capacitive feedback. A transimpedance amplifier is one that converts current to voltage.

FIG. 5 presents a resistive feedback transimpedance amplifier 500. The amplifier 500 of FIG. 5 has two main components: a very high gain amplifier network and a compensation network. In FIG. 5 the compensation network includes feedback resistor $R_F$ 507, while the high gain amplifier network includes Op Amp 501, Op Amp 502, and four gain control resistors labeled $R_1$ 508 and $R_2$ 510. See B. Sakmann and E. Neher, "Single-channel recording," *Plenum Press*, New York, 1995.

In FIG. 5, an enabling/disabling command voltage $V_{CMD}$ 504 is applied to the non-inverting input 506 of Op Amp 501, while the potential across a nanopore sensor, which represents an ionic current 503, is applied to the inverting input 505 of Op Amp 501. The ionic current 503 is amplified by the gain of the high gain of the amplifier 500. The gain of the resistive feedback transimpedance amplifier is thus:

$$\text{Gain} = R_F \times \frac{R_2}{R_1}$$

In the resistive feedback transimpedance amplifiers as shown in FIG. 5, the input-referred noise current is inversely proportional to $R_F$. See J. Kim, G. Wang, W. Dunbar and K. Pedrotti, "An integrated patch-clamp amplifier for ultra-low current measurement on solid-state nanopore device," in Proc. IEEE Int. SoC Design Conf., pp. 424-427, November 2010.

To minimize input noise and to maximize total gain in the resistive feedback transimpedance amplifiers such as shown in FIG. 5, the resistance of feedback resistor $R_F$ 507 must be set to be as large as possible. Therefore, implementing high gain and low noise amplifiers using the resistive feedback configuration on a semiconductor chip is problematic because that high value resistances (at least tens of mega-Ohms) that are suitable for use as feedback resistors $R_F$ 507 require large chip areas. In practical applications the basic resistive feedback amplifier shown in FIG. 5 only allows about 1 to 8 amplifiers to be integrated on a single chip. If only 10 to 100 nanopore sensors are used in a given application the basic resistive feedback amplifier of FIG. 5 is acceptable. However, to maximize nanopore sequencing through-put it is highly desirable to increase the number of nanopore sensors that can operate asynchronously and in parallel. The latest sequencing device from Ion Torrect (now part of Life Technologies) has 1.2 Million addressable measurement wells (but read-length is limited by the use of enzymes for sequencing). Thus if the objective is 1 k-10 k nanopore sensors or more per device, an alternative design or an improvement to the basic resistive feedback amplifier of FIG. 5 may be recommended.

It should be noted that several pseudo-resistor techniques have been developed to reduce the required dimensions to implement large resistor values. See for example, R. R. Harrison and C. Charles, "A low-power low-noise CMOS amplifier for neural recording applications," IEEE Journal of Solid-State Circuits, 38: 958-965, June 2003 and M. Chae, J. Kim, W. Liu, "Fully-differential self-biased bio-potential amplifier," Electron. Lett., vol. 44, no. 24, pp. 1390-1391, November 2008. One drawback of pseudo-resistors is that pseudo-resistors require care to achieve precise resistance desired. A pseudo-resistor is implemented as the resistance between the source and drain of a FET on a die.

In view of the foregoing, a new technique for implementing amplifiers on a die would be beneficial. Such a new technique should enable high density amplifiers on the die. Preferably such techniques would be suitable for use with high through-put nanopore sequencing. Such techniques might be scaled to implement at least 2000 and hopefully at least 5,000 or 10,000 or 20,000 or 30,000 or at least 40,000 nanopore amplifiers on a single die.

SUMMARY OF THE INVENTION

Embodiments include a method that includes a plurality of steps such as measuring, with each of at least one measuring device, an ionic current produced by each of at least one molecule. The method includes connecting the each of the at least one measuring device to each of at least one first operational amplifier. The method includes connecting the at least one first operational amplifier to at least one second operational amplifier. The method also includes configuring the at least one first operational amplifier and the at least one second operational amplifier to amplify the ionic current measured by the at least one measuring device and the first operational amplifier and the second operational amplifier are configured to be a capacitive feedback transimpedance amplifier.

Embodiments include an apparatus that includes at least one measuring device configured to measure an ionic current produced by each of at least one molecule. Embodiments include at least one first operational amplifier configured to accept a first output of each of the at least one measuring device. Embodiments include at least one second operational amplifier configured to accept one or more second output of each of the at least one first operational amplifier, wherein the each of the at least one first operational amplifier and the each of the at least one second operational amplifier are configured to amplify the ionic current measured by the at least one measuring device and the first operational amplifier and the second operational amplifier are configured to be a resistive feedback transimpedance amplifier.

Another embodiment includes a printed circuit board with an array of nanopore sensors. The printed circuit board may include a plurality of integrating operational amplifiers, each amplifier configured to receive data from each of the array of nanopore sensors. The printed circuit board includes at least one differentiating operational amplifier, each configured to receive one or more first outputs of the integrating operational amplifier and the plurality of the first operational amplifiers and the at least one second operational amplifier configured to form a capacitive feedback transimpedance amplifier.

Embodiments are directed to integrating high density nanopore amplifiers on a die. That novel technique can be implemented in a manner that is suitable for high through-put nanopore sequencing.

In one embodiment, an integrated and multiplexed network of amplifiers, that are novel capacitive integrator-differentiator amplifiers with small feedback capacitors $C_f$ and that use pseudo-resistors. In various embodiments, a pseudo-resistor may be a resistor whose resistance is set due to a biasing current to realize a resistance while occupying a small silicon surface area. The pseudo-resistor, which is biased in the subthreshold region, is capable of realizing a large resistance. A wide range of resistances can also be implemented by changing the bias current to the pseudo-resistor. Those patch clamp amplifiers reduce the integrator area while achieving a low input-referred noise current. The network beneficially uses a shared differentiator Op Amp to enable more integrator amplifiers per die.

Alternatively, the present invention enables the use of resistive integrator-differentiator amplifiers that use a multiplexer to enable sharing one differentiator Op Amp.

In either approach the die is configured such that the required pads, ESD networks, amplifiers, and metallization areas are reduced in size.

Those principles of the present invention are incorporated in a patch clamp amplifier comprising an integrating Op Amp having an inverting input that receives current variations from a nanopore sensor. A feedback capacitor shunts the output of the integrating Op Amp to its inverting input. That feedback capacitor is shunted by a high impendence. The output of the integrating Op Amp is applied to the inverting input of a differentiator Op Amp by a first input capacitor and a first input impedance. A second input capacitor and a second input impedance connect the non-inverting input of the differentiator Op Amp to the non-inverting input of the integrating Op Amp. A first resistor connects the output of the differentiator Op Amp to its inverting input while a second resistor connects the non-inverting input of the differentiator Op Amp to ground. The high impedance is a pseudo-resistor.

The principles of the present invention further provide for a multiplexed nanopore sensing network having an integrating first Op Amp, an integrating second Op Amp, and an integrating third Op Amp. A multiplexer receives the outputs of the first, second, and third Op Amps and selects one of them to be an output. Selection is based on applied control data. A differentiator Op Amp receives the selected output from the multiplexer and applies its output to an analog to digital converter. The ADC converts the differentiated output into a digital signal. The control data is applied by a multiplexing control block.

The principles of the present invention further provide for a printed circuit board having an N×M array of nanopore sensors. The outputs of the N×M nanopore sensors are applied as inputs to a multiplexer of a multiplexed nanopore sensing network. The multiplexer outputs a selected one of the N×M nanopore sensor inputs based on received control data. A differentiator Op Amp differentiates the selected output and applies the differentiated signal to an analog to digital converter which converts the differentiated output into a digital signal. The control data is applied to the multiplexer by a multiplexing control block. An output module receives the digital signals from the ADC and outputs them in a suitable format for use by other devices.

In practice the N×M nanopore sensors and the multiplexer share a common ground.

The Nanopore sequencer of the invention, comprises an array of nanopores, wherein each nanopore provides an output (a current variation) that provides the input for a patch clamp amplifier comprising an integrating operational amplifier having an inverting input. The sequencer can be used to sequence or to characterize any linear molecule comprising subunits each of which has a different charge. For example it can be used to characterize a polynucleotide or a polypeptide where the bases or the amino acid residues, respectively, have different charges and therefore provide a characteristic signal when passing through the nanopore.

BRIEF DESCRIPTION OF THE DRAWINGS

The advantages and features of the present invention will become better understood with reference to the following detailed description and claims when taken in conjunction with the accompanying drawings, in which like elements are identified with like symbols, and in which:

DETAILED DESCRIPTION

The presently disclosed subject matter now will be described more fully hereinafter with reference to the accompanying drawings in which one embodiment is shown. However, it should be understood that this invention may take many different forms and thus should not be construed as being limited to the embodiment set forth herein.

All documents and references referred to in this disclosure are hereby incorporated by reference for all purposes. In the figures like numbers refer to like elements throughout. Additionally, the terms "a" and "an" herein do not denote a limitation of quantity, but rather denote the presence of at least one of the referenced items.

International application "Dual Pore Device" (WO 2013/012881) is hereby incorporated by reference in its entirety for all purposes. Additionally, the terms "a" and "an" herein do not denote a limitation of quantity, but rather denote the presence of at least one of the referenced items.

Several embodiments of the nucleotide sequencer are described herein with reference to FIGS. 1 to 15. These embodiments of the nucleotide sequencer provide space-efficient, high throughput amplifiers suitable to be implemented on a high density semiconductor die. The high-density semiconductor die may be suitable for use on a circuit board having an array of nanopore sensors. For example, these embodiments of the nucleotide sequencer are suitable to be implemented as a patch clamp.

Figure 1:
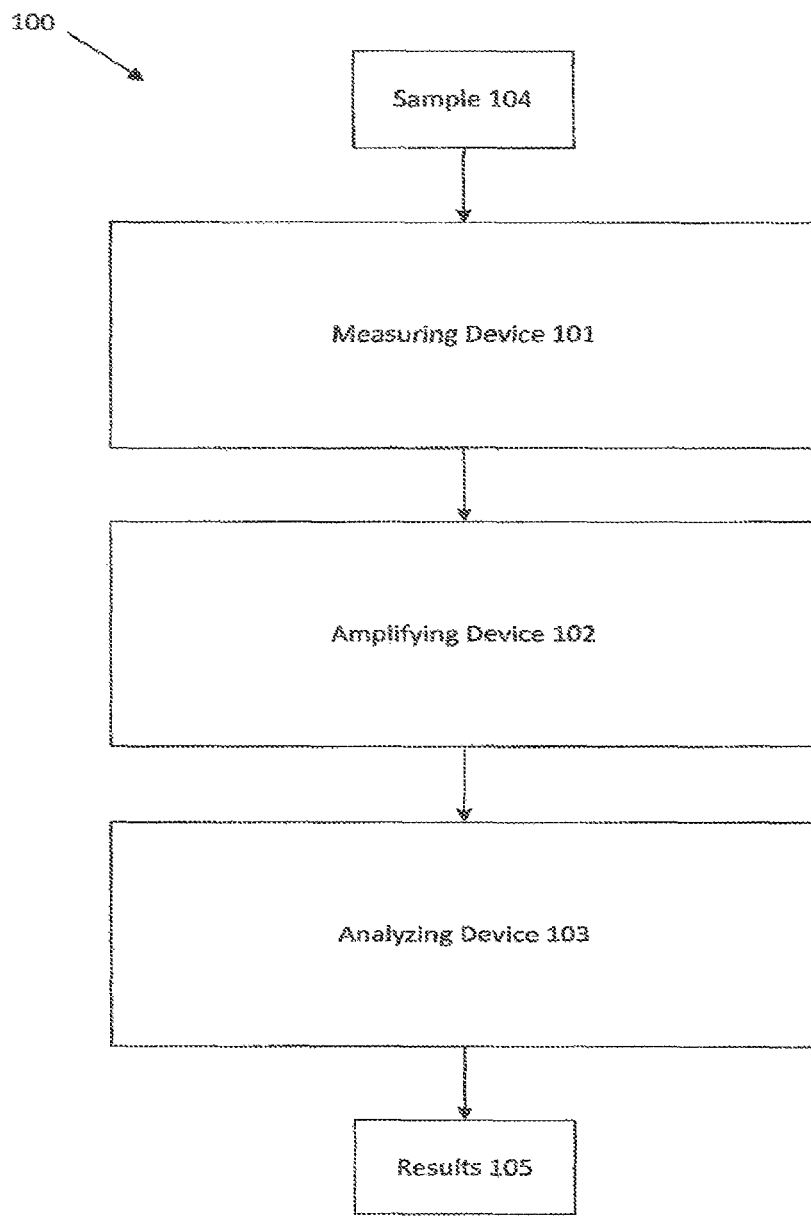
FIG. 1 illustrates exemplified components of a nucleotide sequencer.

As shown in FIG. 1, various embodiments of the nucleotide sequencer 100 include a measuring device 101, an amplifying device 102, and an analyzing device 103. In some embodiments, the measuring device 101 manipulates a molecule as described below. The measuring device 101 may measure the ionic current produced by the molecule sample 104. The amplifying device 102 amplifies the ionic current measured by the measuring device 101 and outputs voltage signals that are representative of the ionic current measured. The analyzing device 103 may perform analysis on the voltage signals, and displays results of the analysis 105.

Figure 2:
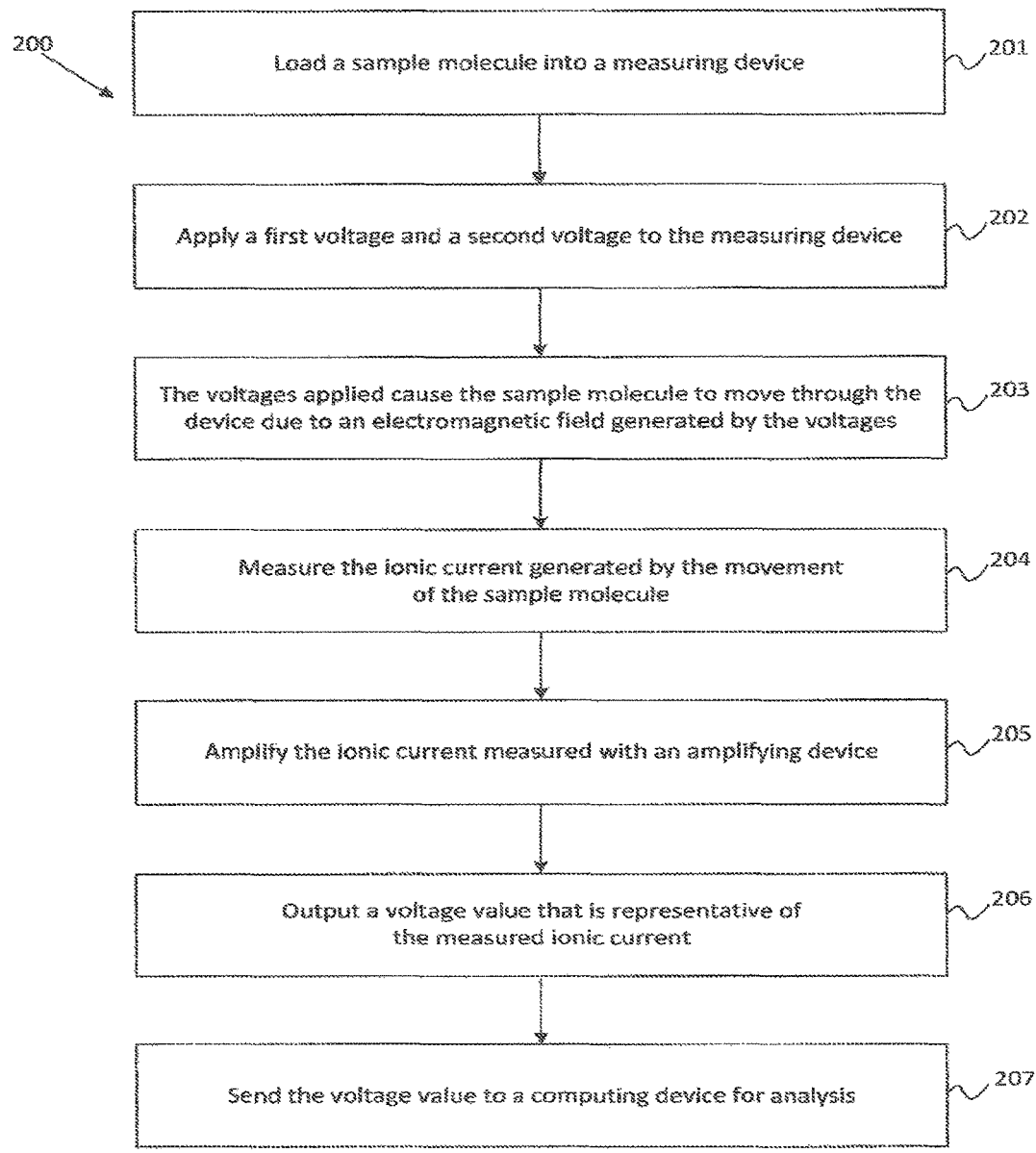
FIG. 2 presents a process performed by the nucleotide sequencer to sequence nucleotides.

FIG. 2 illustrates a process 200 that may be preformed by a nucleotide sequencer to sequence a nucleotide. In step 201, the nucleotide sequencer begins by loading a sample molecule into a measuring device. In one embodiment of the nucleotide sequencer, the measuring device comprises a nanopore or an array of nanopores. Examples of the molecule include but not limited to: a double-stranded DNA, single stranded DNA, double-stranded RNA, single-stranded RNA, or DNA-RNA hybrid. In step 202, a first voltage and a second voltage is applied to the measuring device. In step 203, the voltages applied to the measuring device cause the molecule to move through the measuring device due to an electromagnetic field generated. Next, in step 204, the nanopore or nanopore array measures the ionic current generated by the movement of the molecule as it passes the nanopores. In step 205, the amplifying device of the nucleotide sequencer amplifies the measured ionic current and outputs a voltage value that is representative of the measured ionic current in step 206. Lastly, the amplifying device may send the data that represents the measured currents to a computing device for analysis in step 207. In one embodiment, the computing device sequences the nucleotides based on the data that is received from the amplifying device.

Figure 3:
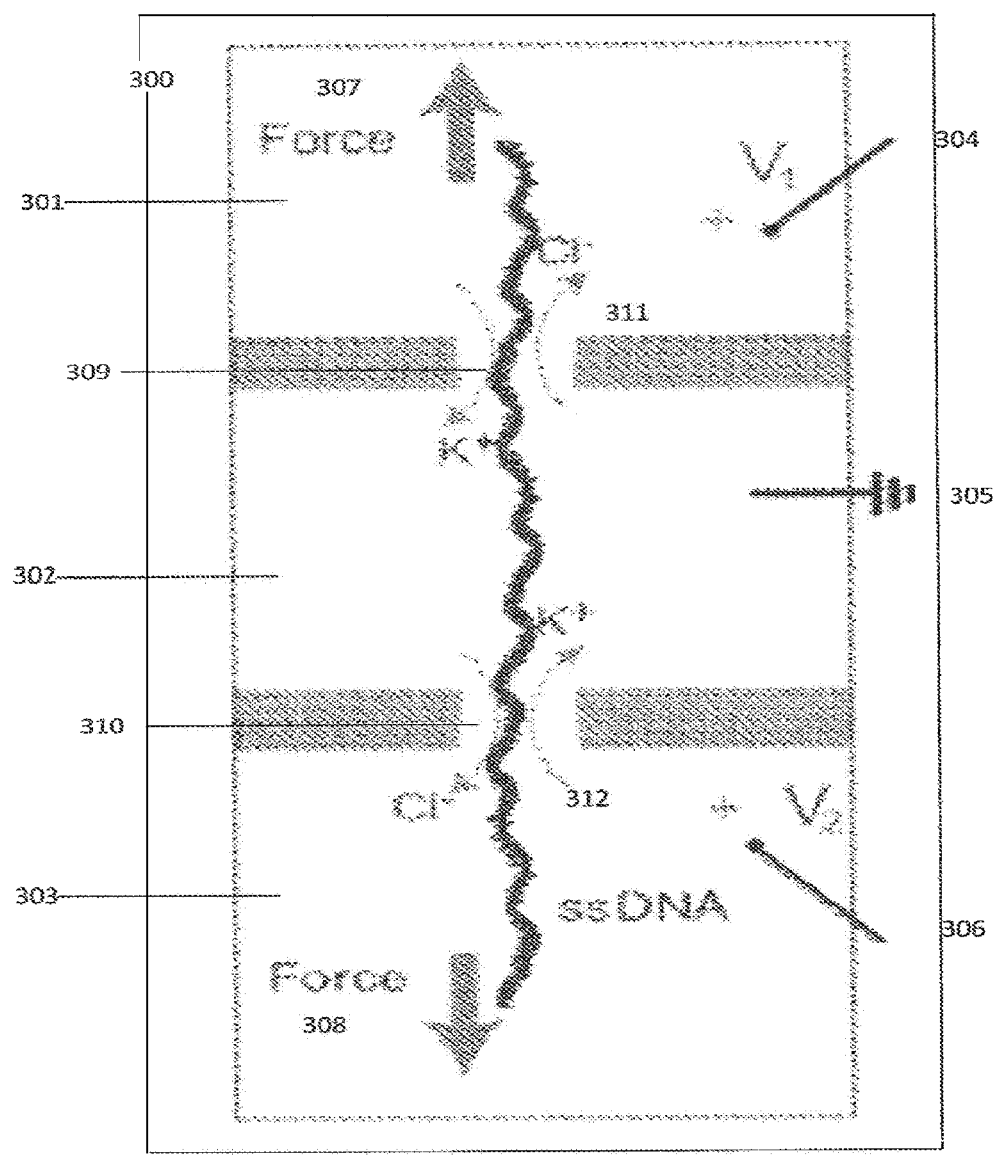
FIG. 3 illustrates an example of a measuring device of the nucleotide sequence, wherein the measuring device uses a nanopore technique.

FIG. 3 shows an example of a measuring device 300. The measuring device comprises an upper chamber 301, a middle chamber 302, and a lower chamber 303. The upper chamber is connected to the middle chamber through a nanopore 309, and the middle chamber 302 is connected to the lower chamber 303 through another nanopore 310. The upper 301 and the lower chambers 302 and 303 are configured to have voltages 304 and 306 applied to them. In some embodiments, a patch clamp or a voltage clamp applies voltages 304 and 306 to the upper and the lower chambers 301 and 303. The middle chamber is grounded 305 with respect to both the upper and the lower chamber 301 and 303. The applied voltages 304 and 306 generate forces 307 and 308, and molecules 311 and 312 move in response to the attraction of the forces.

Figure 4:
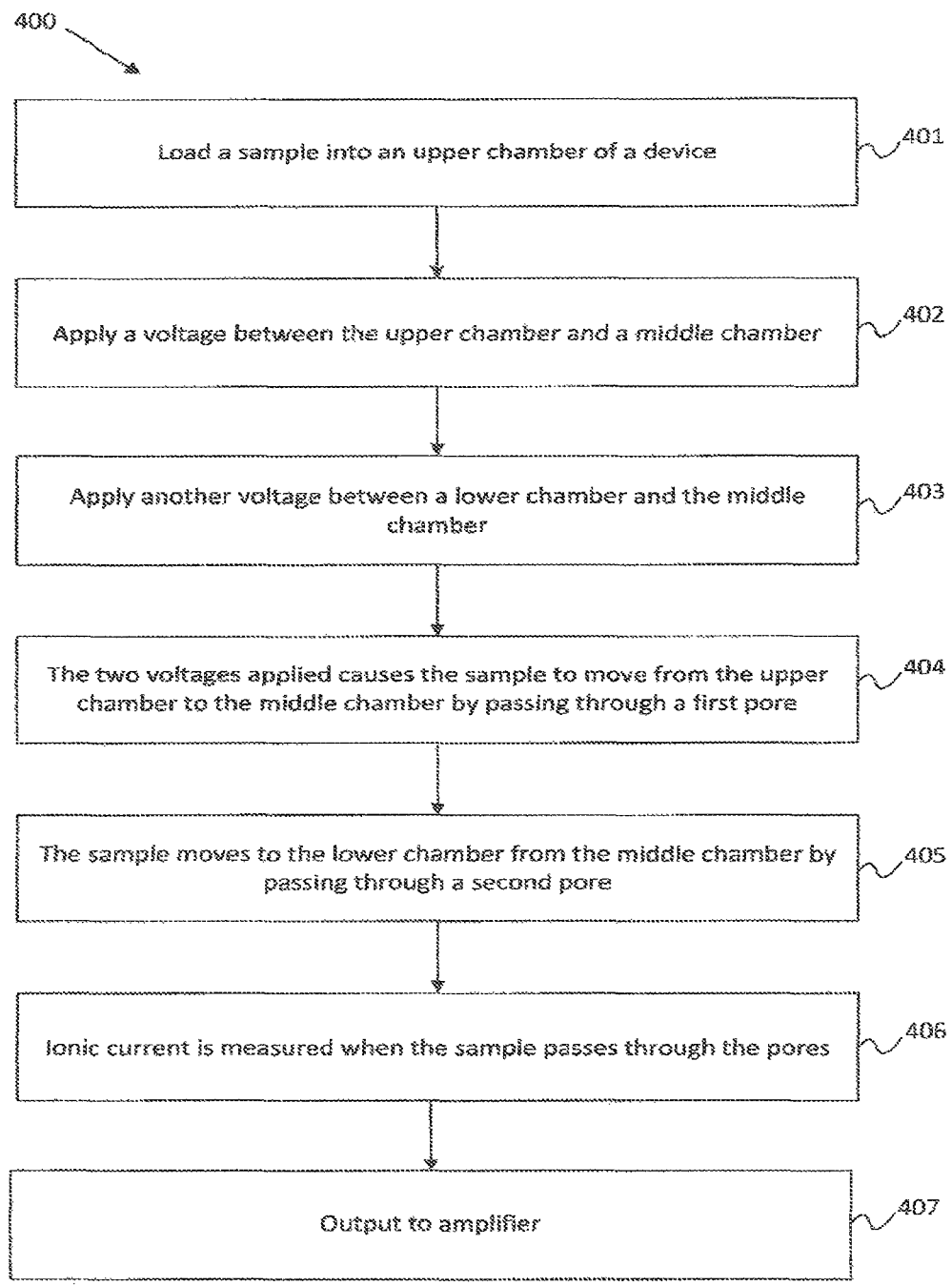
FIG. 4 presents a process that may be implemented by the measuring device to measure ionic current caused by the movement of the nucleotide.

FIG. 4 represents a process 400 through which the measuring device of the nucleotide sequencer takes to measure and output the ionic current caused by the molecule. In step 401, the sample molecule is loaded into the upper chamber of the device. In step 402, a voltage is applied between the upper chamber and the middle chamber. In step 403, another voltage is applied between the lower chamber and the middle chamber. In some embodiments, the voltage applied to the lower chamber and the upper chamber is of a different magnitude. In some embodiments, the voltage of the lower chamber is higher than the voltage of the upper chamber. In other embodiments, the voltage of the upper chamber is higher than the voltage of the lower chamber. In various embodiments, the voltage of one chamber (e.g. upper or lower) is twice the voltage of the other chamber (e.g. upper or lower). In various embodiments, the voltage may be less than twice. In various embodiments, the upper or lower chambers may be both positively charged. In various embodiments, the upper or the lower chambers may be both negatively charged. The voltages can be reset in order to bring out desired pattern of movement of the molecules or calibrated based on a known sample results. As the molecule passes the pores in steps 404 and 405, ionic current measurements are taken in step 406. In one embodiment, a patch clamp sets the voltages and measures the ionic current. In another embodiment, a voltage clamp sets the voltages and measures the ionic current. Lastly, in step 407, the measuring device passes data collected to an amplifying device for amplifying.

Several embodiments are directed to reducing the size of the elements of the amplifying device to enable high-throughput multi-nanopore sensing. Reducing the size of the elements of the amplifying device enables more elements to be placed on a die. For example, a die may have a dimension of 100 µm×100 µm; however, the specific dimensions provided are not meant to be limiting and implementations need not have equal size dimensions.

Figure 6:
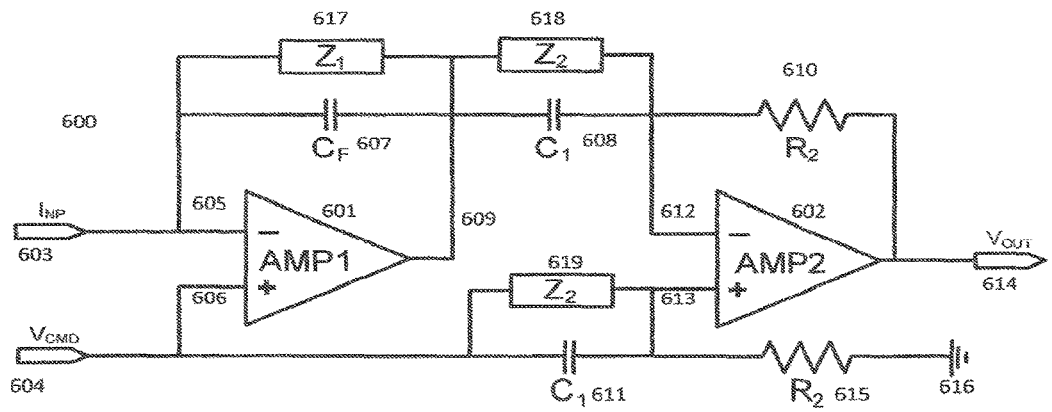
FIG. 6 illustrates a capacitive feedback amplifier that incorporate an integrator-differentiator configuration.

In one embodiment of the nucleotide sequencer, a capacitive feedback transimpedance amplifier is used. FIG. 6 shows an example of such an amplifier 600. The amplifier 600 includes a feedback capacitor $C_F$ 607 in a parallel configuration with a high impendence $Z_1$ 617 between an inverting input 605 and an output 609 of an Op Amp 601. The output 609 of the Op Amp 601 is applied to the inverting input 612 of Op Amp 602 via balancing components comprised of a capacitor $C_1$ 608 and shunting high impedance $Z_2$ 618. Capacitor $C_1$ 608 and the shunting high impedance $Z_2$ 618 are parallel to one another. The non-inverting input 613 of Op Amp 602 is connected to the non-inverting input 606 of Op Amp 601 by a capacitor $C_1$ 611 and shunting high impedance $Z_2$ 619 (the same as applied to the inverting input). An output 614 of Op Amp 602 is connected to the inverting input 612 of Op Amp 602 with a resistor $R_2$ 610. In addition, a ground contact resistance $R_2$ 615 is connected to the non-inverting input 613 of Op Amp 602. A command voltage $V_{CMD}$ 604 is applied to the non-inverting input 605 of Op Amp 601. An ionic current 603 measured by a nanopore sensor is applied to the inverting input 605 of Op Amp 601.

The capacitive feedback transimpedance amplifier in FIG. 6 is implemented in an integrator-differentiator configuration. The integrating portion of the amplifier includes the Op Amp 28, the feedback capacitor $C_F$ 24, and the shunting impedance $Z_1$ 26. The differentiating portion of the amplifier includes the Op Amp 36, the capacitor $C_1$ 30, the impedance $Z_2$ 32, and the resistor $R_2$ 34 is the differentiator. Here, $Z_1$ 26 and $Z_2$ 32 are high impedance paths used to set DC bias. The gain of the integrator-differentiator amplifier is:

$$\text{Gain} = R_2 \times \frac{sC_1 + \frac{1}{Z_2}}{sC_F + \frac{1}{Z_1}}$$

In one embodiment, the amplifier is implemented with impedances $Z_1$ and $Z_2$ that have large impedance (for example, if $Z_1$ and $Z_2$ each has an impedance of 10MΩ, then each of $1/Z_1$ and $1/Z_2$ is 0.0000001, which is negligible in most cases; however, $Z_1$ and $Z_2$ need not to be in that order of magnitude to realize the present embodiment) then the values of $1/Z_1$ and $1/Z_2$ approach close to zero. Therefore, the gain of the amplifier becomes:

$$\text{Gain} = R_2 \times \frac{C_1}{C_F}$$

The above equation shows that the pole in the denominator and the zero in the numerator cancel. This enables the amplifier of FIG. 4 to achieve a wide bandwidth.

In one example, on-chip poly resistors (with resistance in the order of tens of MΩ or GΩ) can be used to realize the high impedance of $Z_1$ 617 and $Z_2$ 618. In various embodiments, on-chip poly resistors may be a plurality resistors formed on the semiconductor die, and they may be used to implement high impedance. The length and width of an on-chip poly resistor is approximately in the 1 µm to 10 µm orders of magnitude. In another examples, reset switches are used in place of $Z_1$ 617 and $Z_2$ 618. If reset switches are used, then means to reduce glitch noises from periodic resetting of the reset switches should be used. In yet another example, pseudo resistors are used to realize high impedance for $Z_1$ 617 and $Z_2$ 618. Pseudo resistors are linear resistances employing NMOS or PMOS transistor in a linear region for the purposes of setting DC paths and reducing the amplifier size. See, for example, R. R. Harrison and C. Charles, "A low-power low-noise CMOS amplifier for neural recording applications," IEEE Journal of Solid-State Circuits, 38: 958-965, June 2003 and G. Ferrari, F. Gozzini, A. Molari and M. Sampietro, "Transimpedance amplifier for high sensitivity current measurements on nanodevices," IEEE J. of Solid-State Circuits, vol. 44, no. 5, pp. 1609-1616, May 2009.

The input-referred noise current of the capacitive feedback transimpedance amplifier 600 shown in FIG. 6 is directly proportional to $C_F$. (See., B. Sakmann and E. Neher, "Single-channel recording," Plenum Press, New York, 1995.) Reducing $C_F$ 607 can not only minimize the integrator area (the headstage) but also achieves a desired low input-referred noise current. Embodiments of the nucleotide sequencer overcome the noise problem caused by resistive feedback transimpedance amplifiers shown in FIG. 5.

Figure 7:
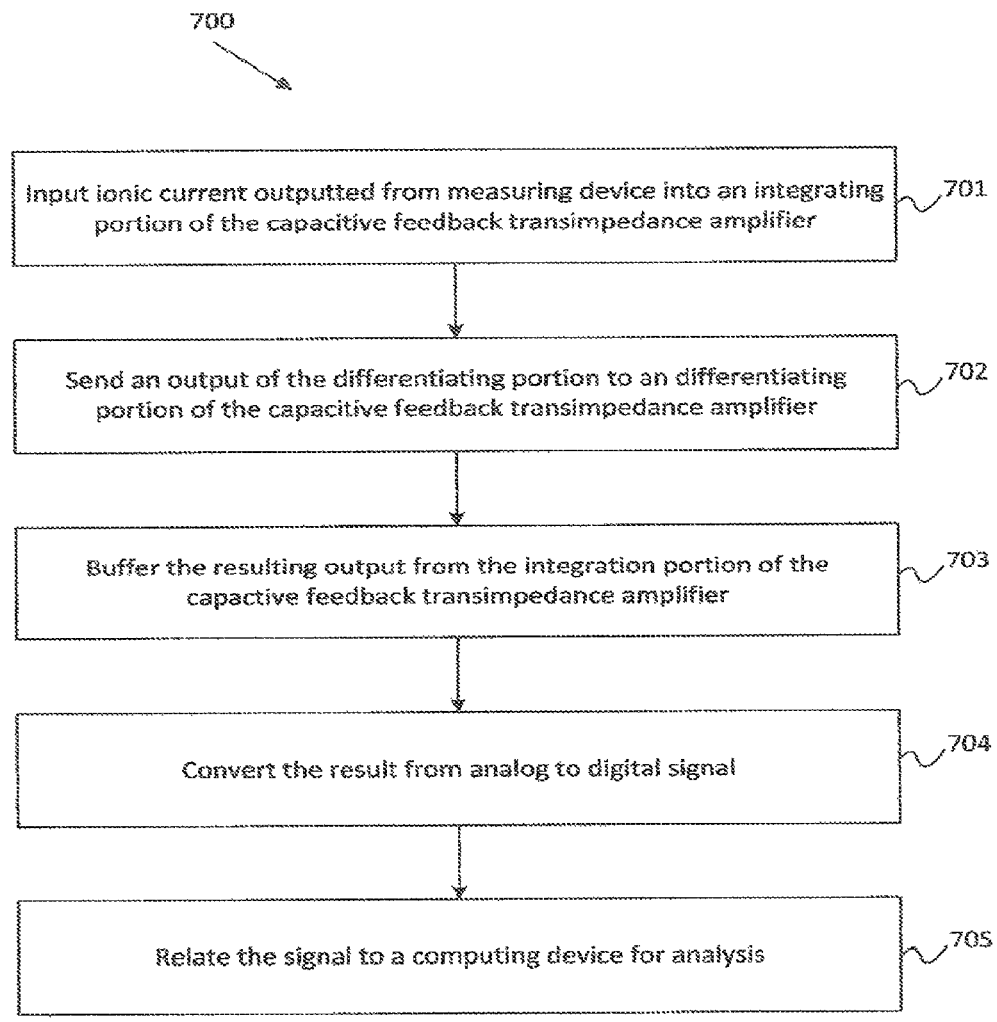
FIG. 7 presents a process that may be performed by the amplifying device to amplify the ionic current received from the measuring device using the capacitive feedback amplifier in the integrator-differentiator configuration.

In one embodiment, the amplifying unit of the nucleotide sequencer uses the capacitive feedback transimpedance amplifier with the integrator-differentiator configuration to amplifying the measured ionic current outputted from the measuring device. FIG. 7 represents a process 700 that amplify the measured ionic current using the amplifying device. In step 701, the integrating portion of the capacitive feedback transimpedance amplifier receives an output ionic current from the measuring device. The measuring device could include an array of nanopore sensors. Then, in step 702, the output from the integrating portion is sent to the differentiating portion of the capacitive feedback transimpedance amplifier. In one approach, an individual differentiating portion is connected to an individual integrating portion. In another approach, multiple integrating portions are connected to one differentiating portion through the use of a multiplexer as discussed below. Given that the amplifier comprises of a transimpedance feedback, the resulting signal is a voltage value instead of a current value. In step 703, the output(s) from the differentiating portion(s) are buffered. In step 704, a digital to analog converter (ADC) converts the analog signal of the buffered output from the differentiating portion of the capacitive feedback transimpedance amplifier to digital signals. In step 705, the digital signal is related to a computing device for analysis. The computing device can be any device with a process. Examples of the computing device include, but not limited to, a smart phone, tablet, personal computer, and laptop. The digital signal can be related to the computing device through a universal serial bus (USB) module, a wireless network, or any other wireless or wireless connection.

Figure 8:
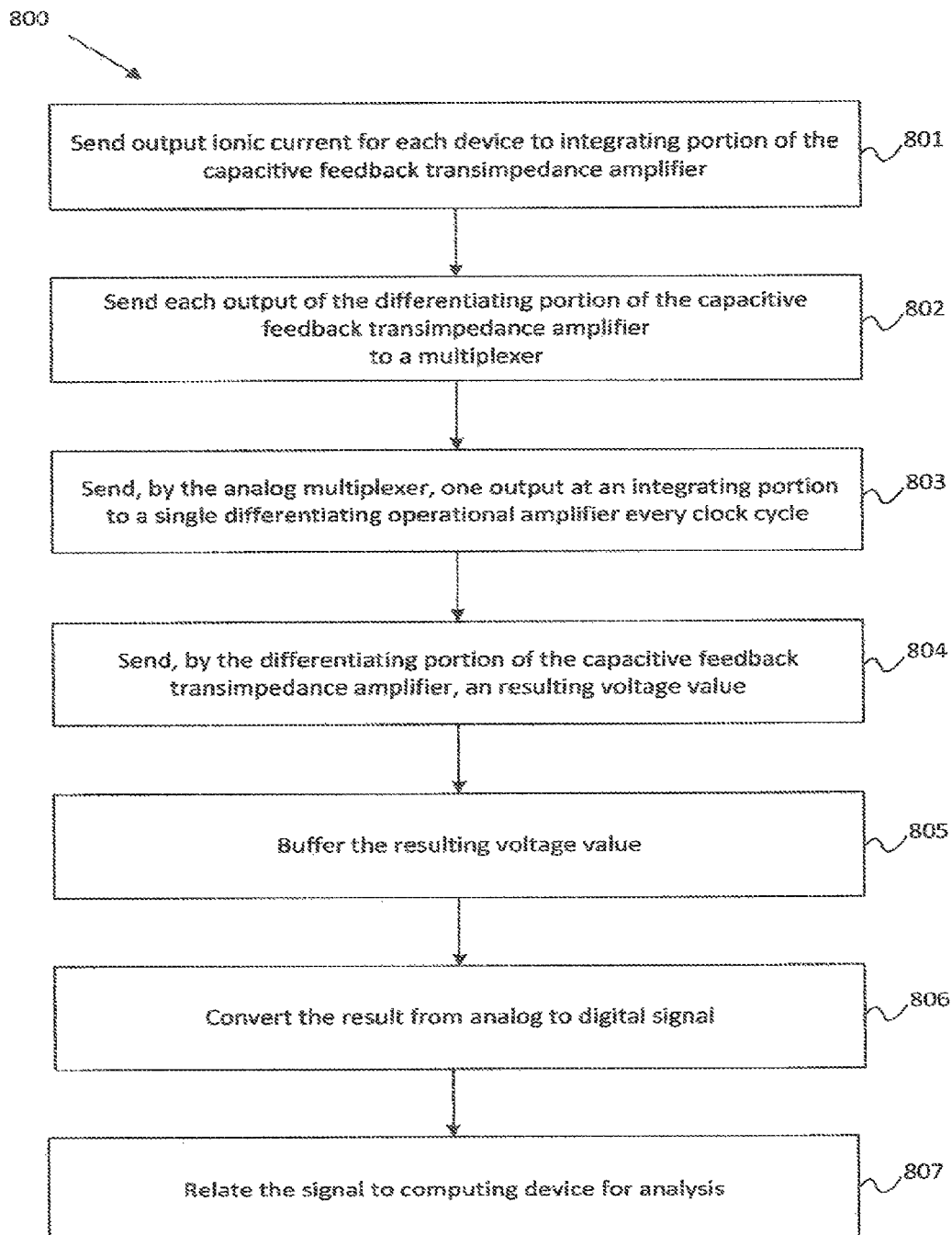
FIG. 8 presents a process that may be performed by the amplifying device to amplify the ionic current received from the measuring device using the capacitive feedback amplifier in the integrator-differentiator configuration and a multiplexer.

In one embodiment, a multiplexer is used to connect a plurality integrating portions of the capacitive feedback transimpedance amplifier to one differentiating portion. In one embodiment, the multiplexer is an analog time division multiplexer. FIG. 8 represents a process 800 that the amplifying device with a multiplexer implementation takes to amplify the ionic current. In step 801, the integrating portion of the capacitive feedback transimpedance amplifier receives an output ionic current from the measuring device. The measuring device could include an array of nanopore sensors. Then, in step 802, the outputs or output signals from the integrating portions are sent to a multiplexer. In step 803, the multiplexer arranges the outputs from the integrating portions so that the multiplexer will send one output at a time to the differentiating portion every clock cycle. Given that the amplifier comprises of a transimpedance feedback, the resulting signal is a voltage value instead of a current value. In step 804, a voltage value is output from the differentiating portion. In step 805, the outputs from the differentiating portion are buffered. In step 806, a digital to analog converter (ADC) converts the analog signal of the buffered output from the differentiating portion of the capacitive feedback transimpedance amplifier to digital signals. In step 807, the digital signal is related to a computing device for analysis. The computing device can be any device with a process. Examples of the computing device include, but not limited to, a smart phone, tablet, personal computer, and laptop. The digital signal can be related to the computing device through a universal serial bus (USB) module, a wireless network, or any other wireless or wireless connection.

Figure 9:
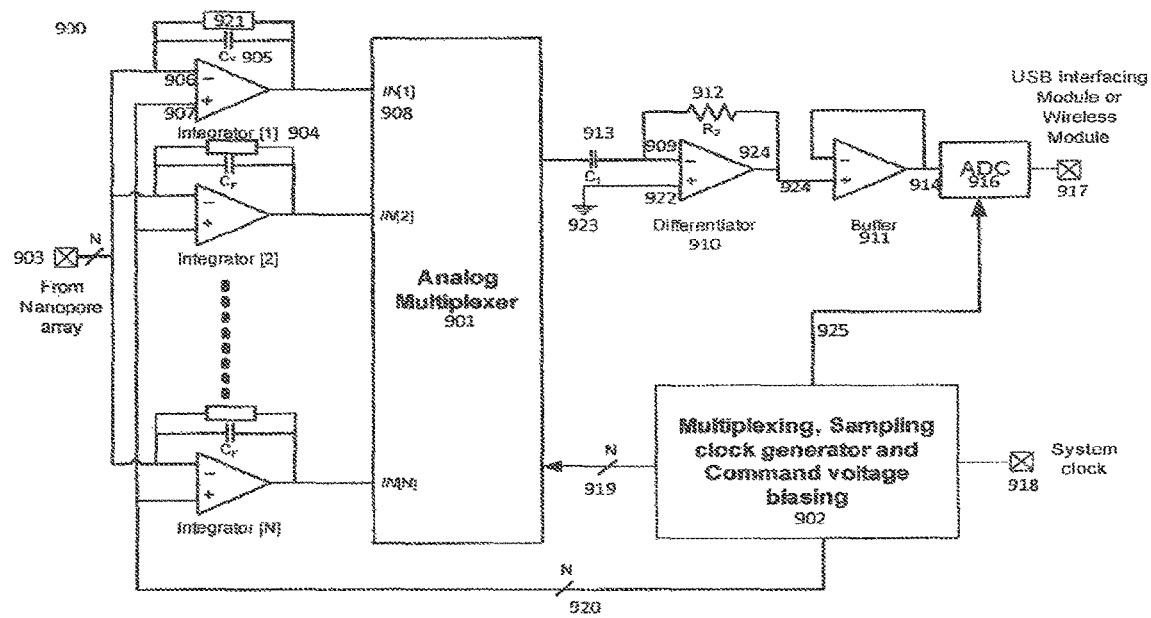
FIG. 9 illustrates a multiplexing network suitable for multi-nanopore sensing based on the capacitive feedback amplifier shown in FIG. 6.

FIG. 9 illustrates an N-integrator capacitive feedback multiplexed configuration based on capacitive feedback transimpedance amplifier with the integrator-differentiator configuration 900. In this example, each of N-number of nanopore sensors 903 are connected to an inverting input 906 of each of N-number of integrating portions 904. An analog multiplexer 901 receives the outputs 908 of each of the N-number of integrating portions 904. Each integrating portions 904 includes a feedback capacitor $C_F$ 905 and a high impedance $Z_1$ 905. In various embodiments each nanopore sensor 903 shares a ground of the analog multiplexer 901, but reference may be made to the ground line 1306 of FIG. 13. Each nanopore 903 cis chamber is connected to one and only one integrating portion 904 while all trans chambers and the analog multiplexer 901 share the same ground.

Still referring to FIG. 9, all integrating portions 904 are turned on when a command voltage (VCMD) is provided on a DC biasing line 919 from a Multiplexing, Sampling Clock Generator, and Command voltage biasing block 902 (hereinafter M-SC-CV block 90). As discussed above, $C_F$ 905 has a capacitance in the picoFarad range to increase the gain while decreasing noise.

Also in FIG. 9, the analog multiplexer 901 selects one of the outputs of the integrating portion 908 and connects that selected output to a capacitor 913 which in turn connects to the inverting input 909. The analog multiplexer applies the selected output to a differentiating portion comprising of a capacitor 913, a differentiator Op Amp 910, and a feedback resistor $R_2$ 912. The non-inverting input 922 of the differentiator Op Amp 910 is grounded 923. The output 924 of the differentiating portion 910 is applied to the non-inverting input 915 of a unity gain buffer Op Amp 911. The output of the buffer Op Amp 911 is applied to an analog to digital converter (ADC) 916 whose output 914 is made available via a USB interfacing module or a wireless module 917.

The differentiating portion 910 processes the outputs 908 of all N-number integrating portions 904 via the analog multiplexer 901. The selected analog multiplexer 901 channel is controlled by signals applied on buss 919 by the M-SC-CV block 902. The analog multiplexer 901 is controlled in accord with a system clock 918 of the M-SC-CV block 902, which is made available on a pad. Only one channel of the analog multiplexer 901 is activated per system clock cycle. The analog multiplexer 901 may take the outputs 908 of the N-number integrating portions and output a signal which combines the N-number integrating portions 904. The M-SC-CV block is connected to the non-inverting inputs of the integrating portions 904 via line 920. Finally the operations of the ADC 916 are also controlled by the M-SC-CV block 902 via a line 925 to avoid signal glitches, induced noise, and/or to synchronize system operations.

Figure 10:
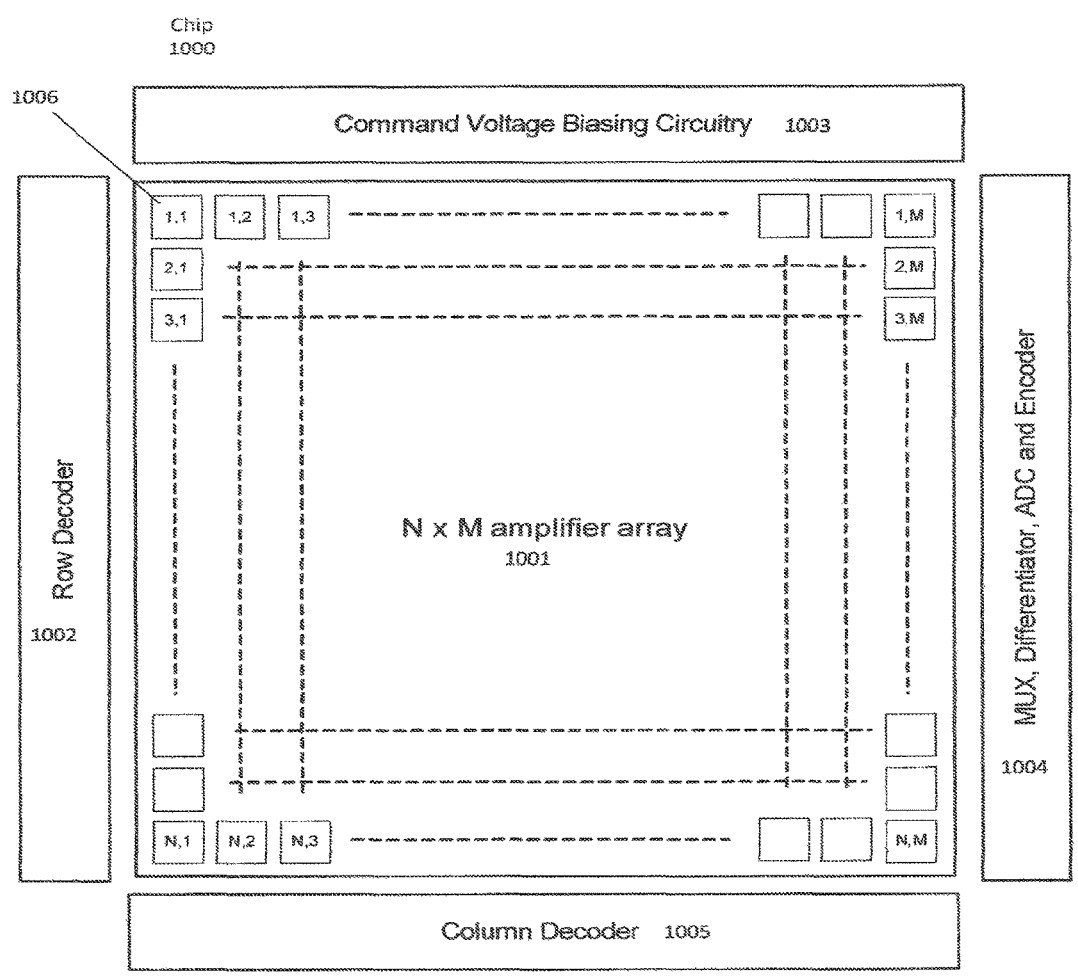
FIG. 10 presents a top-down view of a semiconductor chip that incorporates the multiplexing network shown in FIG. 9.

FIG. 10 presents a top-view layout of an N×M chip that implements the capacitive feedback transimpedance amplifier with a multiplexer shown in FIG. 6 (note: pads are not illustrated for clarity) along 4 sides. The configuration of FIG. 10 arranges N-by-M integrator Op Amp 1006 array 1001 in the center of a chip 1000. The functional blocks 1002, 1003, and 1004 are located around the chip periphery, the functional blocks include a row decoder 1002, command voltage bias circuitry 1003, multiplexer, differentiator, ADC, and encoder block 1004, and column decoder 1005. Pad sizes and locations are however critical to an efficient layout. For example, if 100 Op Amp array 1001 are integrated on the chip, at least 100 pads may be required to access the nanopore array. In that case 25 pads would be located on each side (assuming a 25×25 configuration). If each pad is 100 µm×100 µm with a pitch of 200 µm, 25 pads would occupy 5 mm on each side. Thus the chip would be more than 5 mm×5 mm. As other functional blocks 1002, 1003, 1004, and 1005 are needed and have their own inputs and outputs the number of pads needed increases, which in turn increases the size of the chip. In practice the pad dimensions end up controlling chip density. Therefore, in one embodiment, system may implement the area-efficient pad technique taught by L. Luh, J. Chroma, and J. Draper, "Area-efficient area pad design for high pin-count chips," in Proc. IEEE Ninth Great Lakes Symp. VLSI, pp. 78-81, March 1999. That area-efficient pad technique is used for high pin-count chips.

Figure 11:
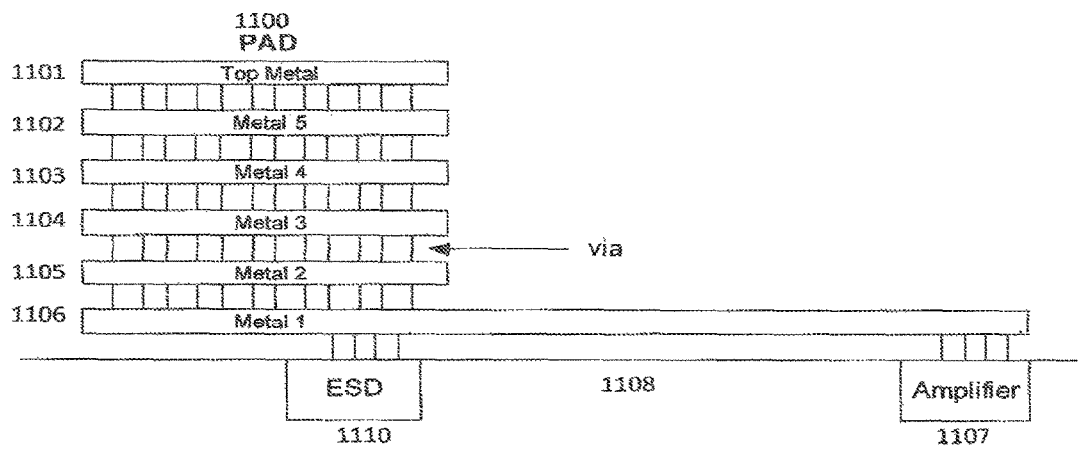
FIG. 11 illustrates a cross-sectional view of a typical pad, ESD network, and amplifier.

FIG. 11 illustrates a cross-sectional structure having a pad 1100 comprised of a top metal layer 1101, a 5th metal layer 1102, a fourth metal layer 1103, a third metal layer 1104, a second metal layer 1105 and a first metal layer 1106. That cross-sectional structure also includes an ESD network 1110 and an amplifier 1107. Because the amplifier 1107 is located in the center of the chip, the amplifier 1107 is connected to the pad 1100 and ESD 1110 through the rather long first metal line 1108. In FIG. 11 it should be understood that the pad 1100 and the ESD 1110 network are placed at the peripherals of the chip.

Figure 12:
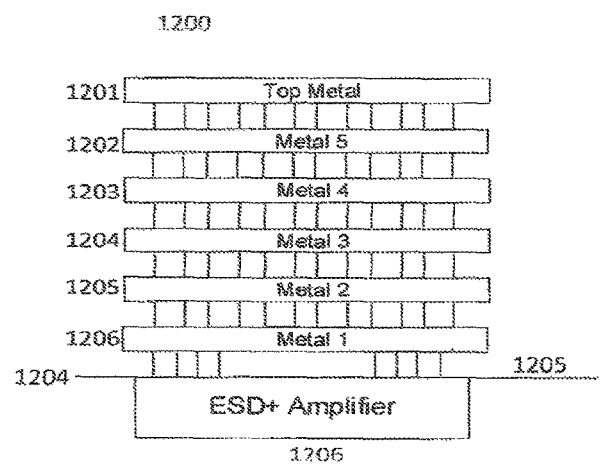
FIG. 12 illustrates a cross-sectional structure of a pad, ESD network, and amplifier for use in the semiconductor chip shown in FIG. 4.

To increase chip density, rather than use the cross-sectional structure shown in FIG. 11, one approach implements the cross-sectional structure illustrated in FIG. 12. As shown in FIG. 12 the cross-sectional structure has a pad 1200 comprised of a top metal layer 1201, a 5th metal layer 1202, a fourth metal layer 1203, a third metal layer 1204, a second metal layer 1205 and a first metal layer 1206. However, the first metal layer 1201 is relatively short. This is achieved by integrating the ESD network and an integrator amplifier as an ESD+Amplifier network 1206 that is placed under the pad 1200 in the center of the chip. This enables a reduced chip size and/or a higher density. Flip-chip bonding can be used to connect the chip to a multi-nanopore array which is located on a printed-circuit board (PCB).

Figure 13:
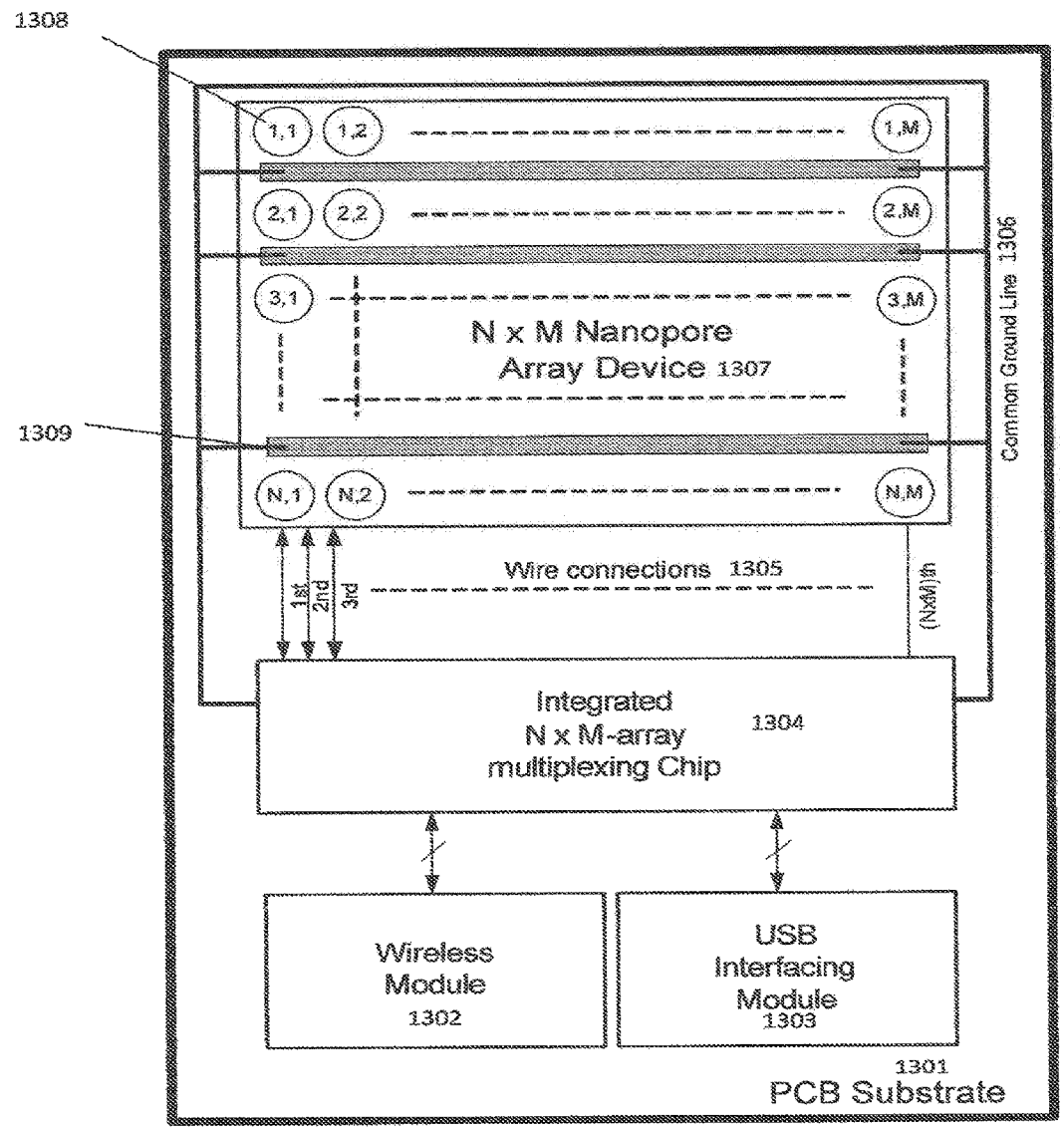
FIG. 13 presents a board-level configuration for multi-nanopore sensing using a multiplexing patch-clamp network chip as shown in FIG. 4.

FIG. 13 present a board-level configuration for multi-nanopore sensing using the inventive multiplexing technique in an integrated N×M array multiplexing chip 1304 and an N×M nanopore sensor array 1307 made of nanopore sensors 1308. The N-by-M nanopore sensor array 1307 has N×M cis chambers but only one trans chamber that is directly connected to the integrated N×M array multiplexing chip 1304 by a common ground line 1306. If the trans reservoir is placed in the top-right corner (beside 1, M chamber), the distance between the trans reservoir and the N, 1 chamber may cause a parasitic resistance. That makes the ground 1309 of the N, 1 chamber different than the ground of the trans reservoir. To reduce the deleterious effects of the parasitic resistance FIG. 13 incorporates a mesh-type trans-reservoir that is connected to the multiplexing chip ground through multiple metal lines 1305. This reduces the line parasitic resistance and normalizes the grounds to a common value.

In FIG. 13, the integrated N×M array multiplexing chip 1304 outputs digital bit streams that are fed to a wireless module 1302 and to a USB interfacing module 1303. Of course, other types of interfaces could be used. The wireless module 1302 wirelessly transmits data into a smart phone, tablet PC, or other receiving device. The USB interfacing module 1303 beneficially can be applied to a personal computer through a USB port.

Figure 15:
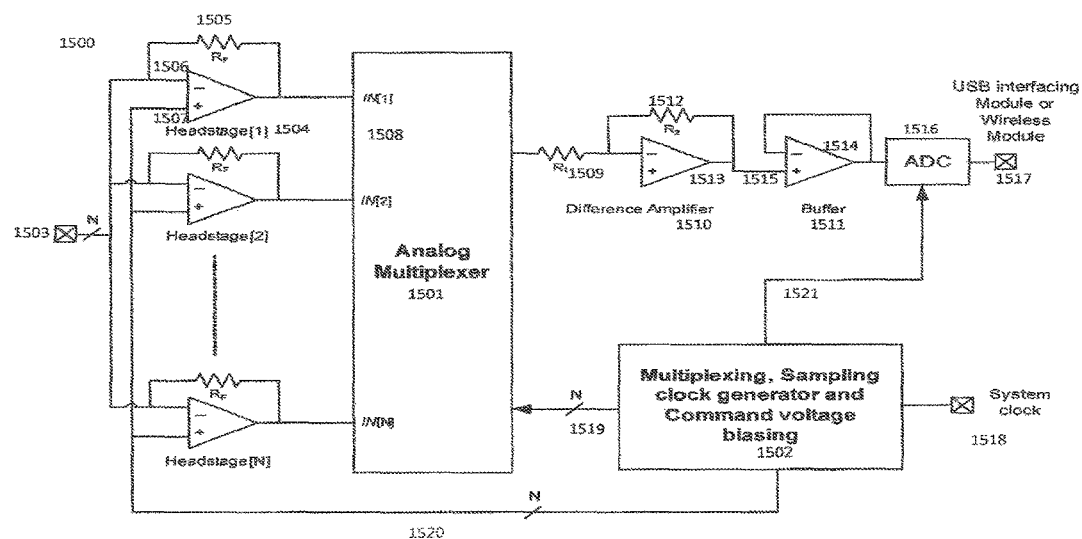
FIG. 15 illustrates a multiplexing multi-nanopore sensing using resistive-feedback transimpedance patch clamp amplifiers.

The overall goal is to realize 1,000 or more patch clamp amplifiers on the N×M array multiplexing chip 1304. However, it is also possible to simply use resistive-feedback amplifiers similar to that shown in FIG. 5 for multi-channel nanopore sensing. In that case, as previously noted the number of amplifier integrated onto a chip is limited by a size of the feedback resistor $R_F$. FIG. 15 illustrates that case.

Figure 14:
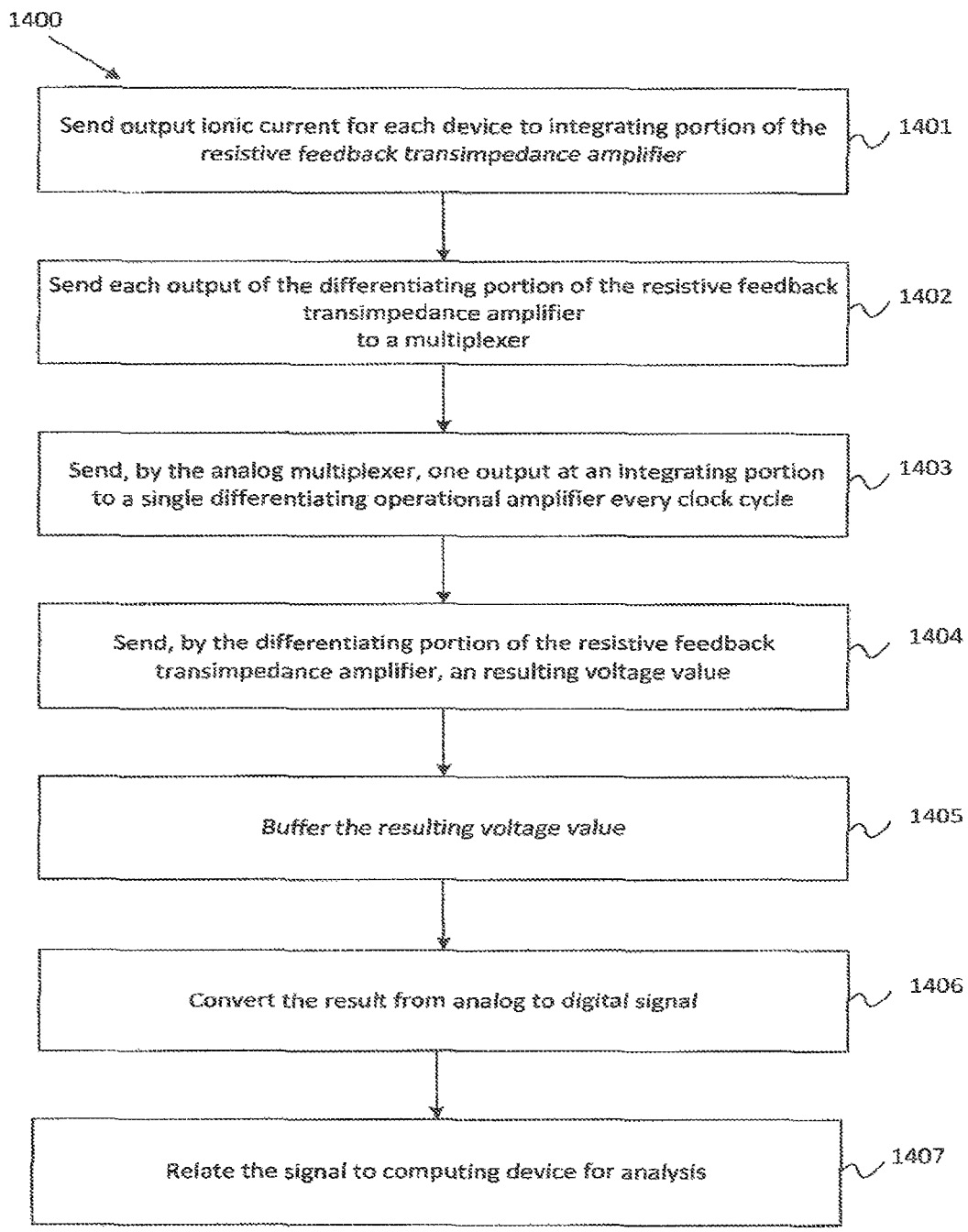
FIG. 14 presents a process that may be performed by the amplifying device to amplify the ionic current received from the measuring device using the resistive feedback amplifier in the integrator-differentiator configuration and a multiplexer.

In various embodiments, the amplifying unit of the nucleotide sequencer uses the resistive feedback transimpedance amplifier with the integrator-differentiator configuration to amplifying the measured ionic current that is output from the measuring device. In various embodiments, the resistive feedback transimpedance amplifier is implemented with a pseudo-resistor. FIG. 14 represents a process 1400 through which the measured ionic current is amplified with the amplifying device using resistive feedback and a multiplexer. In step 1401, the integrating portion of the resistive feedback transimpedance amplifier receives an output ionic current from the measuring device. The measuring device could include an array of nanopore sensors. Then, in step 1402, the outputs from the integrating portions are sent to a multiplexer. In step 1403, the multiplexer arranges the outputs from the integrating portions such that it will send one output at a time to the differentiating portion every clock cycle. In step 1404, the differentiating portion outputs an resulting voltage value. Given that the amplifier comprises of a transimpedance feedback, the resulting signal is a voltage value instead of a current value. In step 1405, the output(s) from the differentiating portion(s) are buffered. In step 1406, a digital to analog converter (ADC) converts the analog signal of the buffered output from the differentiating portion of the resistive feedback transimpedance amplifier to digital signals. In step 1407, the digital signal is related to a computing device for analysis. The computing device can be any device with a process. Examples of the computing device include but not limited to a smart phone, tablet, personal computer, and laptop. The digital signal can be related to the computing device through a universal serial bus (USB) module, a wireless network, or any other wireless or wireless connection.

Figure 5:
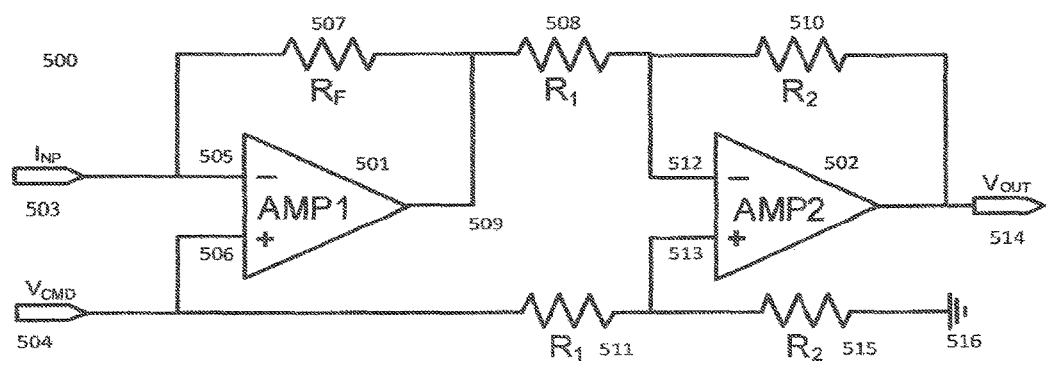
FIG. 5 illustrates a schematic depiction of a resistive feedback amplifier.

FIG. 15 illustrates the use of an analog multiplexer 1501 and a shared difference Op Amp amplifier 1510 with resistive feedback integrator Op Amps 1504 in a manner that still enables a reduction in overall dimensions, which enables more amplifiers per chip. FIG. 15 shows an N-integrator resistive feedback multiplexed configuration 1500 that is based on resistive feedback transimpedance amplifying with integrator-differentiator configuration as shown in FIG. 5. In this example, each of N-number of nanopore sensors 1503 are connected to an inverting input 1506 of each of N-number of integrator Op Amps 1504. Each integrating portion 1504 includes a feedback resistor $R_F$ 1505. Not shown for clarity is that each nanopore sensor 1503 shares the same ground as the analog multiplexer 1501. Each nanopore cis chamber is connected to one and only one integrator Op Amp 1504 while all trans chambers and the analog multiplexer 1501 share the same ground.

Still referring to FIG. 15, all integrator Op Amps 1504 are turned on by a command voltage (VCMD) provided on a DC biasing line 1520 from a Multiplexing, Sampling Clock Generator, and Command voltage biasing block 1502 (herein after M-SC-CV block 520). $R_F$ 1505 is chosen to have a high values in the tens of MOhm or GOhm range. Smaller feedback resistors $R_F$ 1505 enable more Op Amps 1504 but at the cost of gain.

Referring to FIG. 15, the analog multiplexer 1501 selects one of the outputs 1508 of the integrating portions 1504 and connects that selected output to a resistor $R_1$ 1509, which applies the selected output to a gain amplifier Op Amp 1510 and to a feedback resistor $R_2$ 1512. The output 1513 of the gain amplifier Op Amp 1510 is applied to the non-inverting input 1515 of a unity gain buffer Op Amp 1511. The output of 1514 the buffer Op Amp 1511 is applied to an analog to digital converter 1516 whose output is made available on a pad 1517. The pad 1517 might connect to a USB interface module or a wireless module or some other type of output.

The gain amplifier Op Amp 1510 is shared by all integrator Op-Amps 1540 via the analog multiplexer 1510 and gain controls are used to adjust the actual value of $R_2$ 1512. The selected analog multiplexer 1501 channel is controlled by signals applied on buss 1519 by the M-SC-CV block 1520. The analog multiplexer 1501 is controlled in accord with a system clock of the M-SC-CV block 1502, which is made available on a pad 1518. Only one channel of the analog multiplexer 1501 is activated per system clock cycle. Finally, the operation of the analog-to-digital converter (ADC) 1516 is also controlled by the M-SC-CV block 1502 via a line 1521 to avoid signal glitches, induced noise, and/or to synchronize system operations.

Comparing FIG. 15 with FIG. 9, in FIG. 15 the feedback capacitors $C_F$ 905 and $C_1$ 913 of FIG. 8 are replaced with resistors $R_F$ 1501 and $R_1$ 1509. Since the feedback resistors $R_F$ are large, tens of MOhms or Giga ohms, the number of amplification channel is restricted. Using pseudo resistors enable the number of channels to be increased. As shown, the multiplexing electronics in FIG. 15 can be adopted to incorporate the same techniques which previously described for the multiplexing electronics using integrator-differentiator architecture.

Amplifier compensation is important. One approach to compensation is found in J. Kim, K. D. Pedrotti and W. B. Dunbar, "On-chip patch-clamp sensor for solid-state nanopore applications," Electronics Letters, vol. 47, no. 15, pp. 844-846, July 2011. That compensation technique reduces and avoids transient delays caused by input parasitic capacitances that occur when the command voltages used for DNA motion control during nanopore sensing change. Such compensation techniques can increase the number of amplification channels on a given size chip. Other compensation techniques are also known, see for example B. Sakmann and E. Neher, "Single-channel recording," Plenum Press, New York, 1995 and P. Weerakoon, and et al., "An integrated patch-clamp potentiostat with electrode compensation," IEEE Trans. on biomedical circuit and system, vol. 3, April 2009. However, those teaching use rather complex structures that occupy a fair amount of chip area. This tends to limit the number of amplification channel on the chip. Thus, the teachings of J. Kim, K. D. Pedrotti and W. B. Dunbar show compensation technique in the multiplexing electronics.

Therefore, it is to be understood that while the figures and the above description illustrate the present invention, they are exemplary only. They are not intended to be exhaustive or to limit the invention to the precise forms disclosed. Obviously many modifications and variations are possible in light of the above teaching. Therefore, the present invention is to be limited only by the appended claims.

The invention claimed is:

1. A patch clamp amplifier, comprising:
    an integrating operational amplifier having a first inverting input for receiving current from a nanopore sensor, said integrating operational amplifier further having a first non-inverting input and a first output;
    a feedback capacitor connecting said first output to said first inverting input;
    a feedback impedance in parallel with said feedback capacitor;
    a differentiator operational amplifier having a second inverting input, a second non-inverting input, and a second output;
    a first input capacitor connecting said second inverting input to said first output;
    a first input impedance in parallel with said first input capacitor;
    a second input capacitor connecting said second non-inverting input to said first non-inverting input;
    a second input impedance in parallel with said second input capacitor;
    a first resistor connecting said second output to said second inverting input; and
    a second resistor connecting said second non-inverting input to ground;
    wherein said feedback impedance is provided by a pseudo-resistor or an on-chip poly resistor.

2. The patch clamp amplifier of claim 1, wherein said first input capacitor and said second input capacitor have the same capacitance.

3. The patch clamp amplifier of claim 1, wherein said first non-inverting input of said integrating amplifier receives a command voltage.

4. The patch clamp amplifier of claim 1, wherein said patch clamp amplifier is a transimpedance amplifier.

5. The patch clamp amplifier of claim 4, wherein said transimpedance amplifier is a capacitive feedback transimpedance amplifier configured as an integrator-differentiator, wherein a first stage (AMP1, $C_F$, $Z_1$) is an integrator and a second stage (AMP2, $C_1$, $R_2$, $Z_2$) is a differentiator, and wherein $Z_1$ and $Z_2$ are high impedance paths configured to set DC bias.

6. The patch clamp amplifier of claim 5 wherein each of $Z_1$ and $Z_2$ is an on-chip poly resistor.

7. The patch clamp amplifier of claim 6 wherein both the length and the width of the on-chip poly resistor is between 1μm to 10μm.

8. The patch clamp amplifier of claim 5 wherein $Z_1$ and $Z_2$ each has an impedance in the order of tens of MΩ or GΩ.

9. The patch clamp amplifier of claim 5 wherein each of $Z_1$ and $Z_2$ is a pseudo resistor.

10. The patch clamp amplifier of claim 9 wherein each of $Z_1$ and $Z_2$ comprises a linear resistance comprising an NMOS or PMOS transistor.

11. The patch clamp amplifier of claim 8 wherein $Z_1$ and $Z_2$ each has an impedance in the order of tens of MΩ or GΩ wherefore the patch clamp amplifier's total gain may be calculated as $$\text{Gain} = R_2 \times \frac{C_1}{C_F}$$

thereby enabling the patch clamp amplifier to achieve a wide bandwidth.

12. The patch clamp amplifier of claim 1 wherein said feedback impedance is provided by an on-chip poly resistor.

13. The patch clamp amplifier of claim 1 wherein said feedback impedance is provided by a pseudo resistor.

* * * * *